US010863955B2

(12) United States Patent
Naylor et al.

(10) Patent No.: US 10,863,955 B2
(45) Date of Patent: Dec. 15, 2020

(54) COORDINATED MOTION OF A ROTATING 2D X-RAY IMAGER AND A LINEAR ACCELERATOR

(71) Applicant: Accuray Incorporated, Sunnyvale, CA (US)

(72) Inventors: Michael P. Naylor, Sunnyvale, CA (US); Matthew Core, San Jose, CA (US); Petr Jordan, Redwood City, CA (US); Calvin R. Maurer, Jr., San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 97 days.

(21) Appl. No.: 15/862,477

(22) Filed: Jan. 4, 2018

(65) Prior Publication Data

US 2018/0192978 A1 Jul. 12, 2018

Related U.S. Application Data

(60) Provisional application No. 62/443,582, filed on Jan. 6, 2017.

(51) Int. Cl.
*A61B 6/10* (2006.01)
*A61B 6/00* (2006.01)
(Continued)

(52) U.S. Cl.
CPC ............ *A61B 6/4458* (2013.01); *A61B 6/032* (2013.01); *A61B 6/102* (2013.01); *A61B 6/4007* (2013.01);
(Continued)

(58) Field of Classification Search
CPC ........... A61B 6/00; A61B 6/10; A61B 6/4458; A61B 6/102; A61B 6/44; A61B 6/4417;
(Continued)

(56) References Cited

U.S. PATENT DOCUMENTS

2006/0002630 A1   1/2006   Fu et al.
2011/0058647 A1   3/2011   Star-Lack et al.
(Continued)

FOREIGN PATENT DOCUMENTS

CN   104605882 A   5/2015
CN   205411197 U   8/2016
(Continued)

OTHER PUBLICATIONS

Int'l Search Report and Written Opinion of the ISA/EP in PCT/US2018/012662 dated Jul. 2, 2018; 11 pgs.

*Primary Examiner* — Jurie Yun
(74) *Attorney, Agent, or Firm* — Womble Bond Dickinson (US) LLP

(57) ABSTRACT

A method includes determining a first set of positions for a volumetric imager and determining a second set of positions for a linear accelerator (LINAC), during radiation treatment delivery. The method further includes determining a set of radiation beam directionalities of the LINAC, wherein for each of the second set of positions for the LINAC a radiation beam corresponds to a radiation beam directionality. The method further includes generating instructions for the volumetric imager based on the first and the second set of positions, the radiation beam directionalities, and a treatment time constraint to avoid a collision between the volumetric imager and the LINAC and between the volumetric imager and the radiation beam, wherein the instructions include physical locations of the volumetric imager and timing values corresponding to the physical locations. The method further includes operating the volumetric imager during the radiation treatment delivery according to the set of instructions.

21 Claims, 11 Drawing Sheets

(51) Int. Cl.
*A61N 5/10* (2006.01)
*B25J 9/04* (2006.01)
*A61B 6/03* (2006.01)
*G02B 30/54* (2020.01)
*G21K 1/02* (2006.01)
*H05H 9/00* (2006.01)
*A61B 8/08* (2006.01)
*A61B 34/20* (2016.01)

(52) U.S. Cl.
CPC .......... *A61B 6/4014* (2013.01); *A61B 6/4266* (2013.01); *A61B 6/4435* (2013.01); *A61B 6/4476* (2013.01); *A61B 6/486* (2013.01); *A61B 6/5235* (2013.01); *A61N 5/1049* (2013.01); *A61N 5/1067* (2013.01); *A61N 5/1083* (2013.01); *B25J 9/04* (2013.01); *G02B 30/54* (2020.01); *G21K 1/025* (2013.01); *A61B 6/4085* (2013.01); *A61B 6/4464* (2013.01); *A61B 6/466* (2013.01); *A61B 6/5264* (2013.01); *A61B 8/5276* (2013.01); *A61B 2034/2065* (2016.02); *A61N 5/1037* (2013.01); *A61N 5/1081* (2013.01); *A61N 2005/1054* (2013.01); *A61N 2005/1061* (2013.01); *A61N 2005/1072* (2013.01); *H05H 9/00* (2013.01)

(58) Field of Classification Search
CPC .......... A61B 6/542; A61B 6/58; A61B 6/588; A61B 6/587; A61N 5/00; A61N 5/10; A61N 5/1049; A61N 5/1081; A61N 5/103; A61N 5/1048; A61N 5/1075; A61N 5/1077; A61N 5/1064; A61N 2005/1061; B25J 9/04; H05H 9/00
USPC .......... 378/62, 65, 117, 197, 207, 210, 901
See application file for complete search history.

(56) References Cited

U.S. PATENT DOCUMENTS

| | | |
|---|---|---|
| 2012/0035470 A1 | 2/2012 | Kuduvalli et al. |
| 2014/0046212 A1 | 2/2014 | Deutschmann |
| 2014/0050297 A1 | 2/2014 | Mostafavi |
| 2016/0303400 A1 | 10/2016 | Maurer, Jr. |

FOREIGN PATENT DOCUMENTS

| | | |
|---|---|---|
| DE | 10139934 A1 | 3/2003 |
| EP | 2630989 A1 | 8/2013 |
| WO | 2015127970 A1 | 9/2015 |
| WO | 2016094284 A1 | 6/2016 |

COORDINATED MOTION OF A ROTATING 2D X-RAY IMAGER AND A LINEAR ACCELERATOR

PRIORITY CLAIM

This application claims the benefit of U.S. Provisional Application No. 62/443,582 filed on Jan. 6, 2017, the entire contents of which are hereby incorporated by reference.

TECHNICAL FIELD

The present disclosure relates to coordination of intrafraction imaging and radiation treatment delivery.

BACKGROUND

In radiation treatment, doses of radiation delivered via a radiation treatment beam from a source outside a patient's body are delivered to a target region in the body, in order to destroy tumorous cells. Typically, the target region consists of a volume of tumorous tissue. During radiation treatment, care must be taken to ensure that collisions do not occur between the various radiation treatment delivery components, as well as between radiation treatment beams and the radiation treatment components.

BRIEF DESCRIPTION OF THE DRAWINGS

The present disclosure will be understood more fully from the detailed description given below and from the accompanying drawings of various implementations of the disclosure.

DETAILED DESCRIPTION

Described herein are embodiments of methods and apparatus for coordinated motion of a rotating 2D x-ray imager and a linear accelerator.

Embodiments of this disclosure are directed to methods for using intrafraction volumetric imaging during a radiation treatment. Embodiments of the present disclosure may be used with a radiation treatment delivery system such as the CyberKnife® radiosurgery system that includes stereo x-ray imaging capability. Alternatively, other types of radiation treatment delivery systems (e.g., gantry based, helical based, etc.) may be used.

In one embodiment, a radiation treatment system includes a linear accelerator (LINAC) 1201 that acts as a radiation treatment source. It is important to ensure that during the successive positionings of the LINAC during a treatment, that the robotic system and a treatment beam of the LINAC do not collide with other objects (e.g., other imaging devices, such as a volumetric imager). An obstacle detection and collision avoidance system, such as that described herein, would therefore be desirable in radiation treatment systems such as the CyberKnife® radiation treatment system.

Figure 1A:
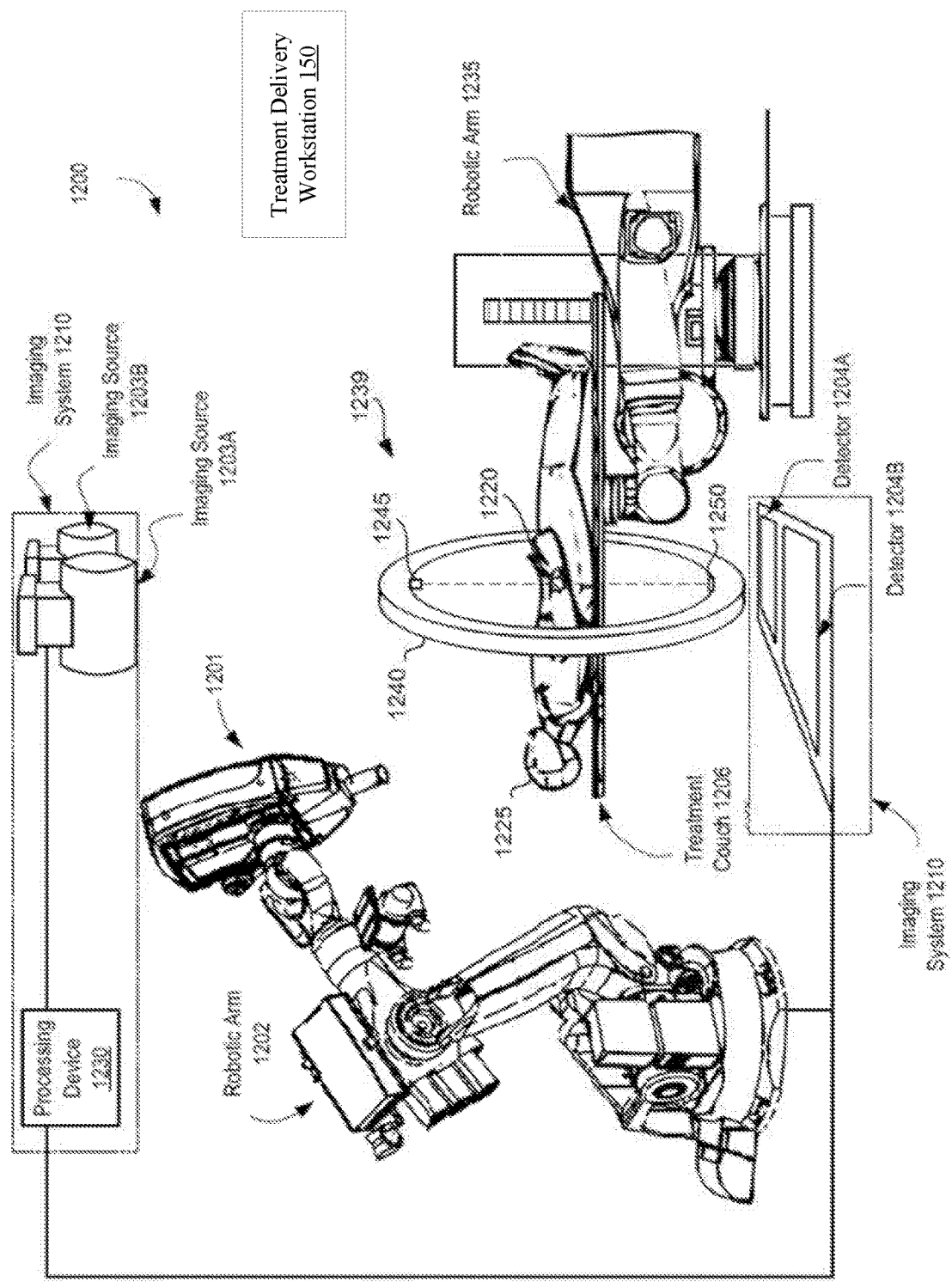
FIG. 1A illustrates a radiation treatment system that may be used in accordance with embodiments described herein.

The use of a volumetric imaging system (e.g., the med-Photon ImagingRing System (IRS)) with a radiation treatment delivery system (e.g., the CyberKnife® radiation treatment system) as shown in FIG. 1A enables new image registration and image tracking opportunities. Worth noting, the term "tracking" used herein may refer to both tracking a treatment target in the treatment planning stages (e.g., determining a location of the treatment target) as well as tracking the treatment target during treatment (e.g., actively updating a location of the treatment target). While the volumetric imaging system (e.g., 1239) may provide superior anatomical information and robust patient alignment, the stereoscopic x-ray imaging system (e.g., 1210) enables frequent intrafraction imaging and tracking. In an alternative embodiment, a radiation therapy device with an integrated in-room diagnostic computer tomography (CT) may be used. With an in-room diagnostic CT, the patient is physically moved (e.g., using a robotic couch) between an in-room diagnostic scanner and the radiation treatment delivery system.

As used herein, "registration" (also referred to herein as "image registration") of medical images refers to the determination of a mathematical relationship between corresponding anatomical or other features (e.g. fiducials) appearing in those medical images. In one embodiment, patients may be imaged multiple times, either with a single modality, or with different modalities. On step when interpreting and comparing image sets is the establishment of correspondence between different points in the multiple images. Image registration is the process of computing a mapping or transformation between coordinates in one image space and those in another. This transformation results in the same anatomical points in different image sets being mapped to each other, and can be used to fuse image sets in order to use the combined imaging information for diagnosis and treatment.

Image registration and fusion may be useful in a variety of contexts, including when combining complementary structural information such as soft tissue from MR with bone from CT. Image fusion is also very useful for interpreting functional imaging. When functional PET or fMR images are fused with high-resolution anatomical images, the functional properties can be linked to the anatomical structures in which they occur.

Registration can include, but is not limited to, the determination of one or more spatial, alignment or intrafraction transformations that, when applied to one or both of the medical images, would cause an overlay of the corresponding anatomical features. The spatial or alignment or intrafraction transformations can include rigid-body transformations and/or deformable transformations and can, if the medical images are from different coordinate systems or reference frames, account for differences in those coordinate systems or reference frames.

Image registration in general may involve computation of similarity values or, equivalently, difference values (e.g., cross correlation, entropy, mutual information, gradient correlation, pattern intensity, gradient difference, image intensity gradients) that are evaluated to determine a spatial transformation between a target's location in a planning room image and a target's location in a treatment room image. Other methods of image registration may be utilized. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Various image registration methods may be utilized with the embodiments described herein. In one example, point-based registration may be used. Points are simple geometrical features that can be used for medical image registration. Point-based registration involves determining the 3-D coordinates of corresponding points in the two images and computing the transformation that best aligns these points.

In another embodiment, surface-based registration may be used. The 3-D boundary or surface of an anatomical object or structure is a geometrical feature that can be used for medical image registration. Surface-based image registration methods may involve determining corresponding surfaces in the two images and computing the transformation that best aligns these surfaces. Whereas point-based registration involves aligning a generally small number of corresponding fiducial points, surface-based registration involves aligning a generally much larger number of points for which no point correspondence information is available.

In another embodiment, intensity-based registration may be used. Intensity-based registration may involve calculating a transformation between two images using a measure of alignment based only on the values of the pixels or voxels in the images. In other embodiments, other methods of image registration may be used.

The term alignment transformation (e.g., volumetric alignment) refers herein to a transformation between a first coordinate system (for example and not by way of limitation a planning image coordinate system of a patient) and a second coordinate system (a treatment room coordinate system) whereby the alignment transformation determines the location of a target in the second coordinate system relative to the first coordinate system, for example and not by way of limitation at the time of patient setup prior to commencement of the treatment fraction.

The term intrafraction transformation refers herein to a transformation between the first coordinate system and the second coordinate system whereby the intrafraction transformation determines the location of the target in the first coordinate system relative to the second coordinate system following commencement of the procedure, for example and not by way of limitation during the treatment fraction.

The term target may refer to one or more fiducials near (within some defined proximity to) a treatment area (e.g., a tumor). In another embodiment a target may be a bony structure. In yet another embodiment a target may refer to soft tissue of a patient. A target may be any defined structure or area capable of being identified and tracked, as described herein.

There is a need to improve on image registration methods to increase the accuracy and computational efficiency in locating a target in one or more images, and thereby more accurately and efficiently determine the spatial transformation between the target's location in a treatment room reference frame relative to a treatment planning image reference frame.

FIG. 1A illustrates a radiation treatment system 1200 that may be used in accordance with embodiments described herein. As shown, FIG. 1A illustrates a configuration of a radiation treatment system 1200. In the illustrated embodiments, the radiation treatment system 1200 includes a linear accelerator (LINAC) 1201 that acts as a radiation treatment source. In one embodiment, the LINAC 1201 is mounted on the end of a robotic arm 1235 having multiple (e.g., 5 or more) degrees of freedom in order to position the LINAC 1201 to irradiate a pathological anatomy (e.g., target 120) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system as described below.

LINAC 1201 may be positioned at multiple different nodes (predefined positions at which the LINAC 1201 is stopped and radiation may be delivered) during treatment by moving the robotic arm 1235. At the nodes, the LINAC 1201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 103A, 1203B and/or x-ray detectors 1204A, 1204B may be mobile, in which case they may be repositioned to maintain alignment with the target 120, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1A, the image-guided radiation treatment system 1200 may further be associated with a treatment delivery workstation 150. The treatment delivery workstation may be remotely located from the radiation treatment system 1200 in a different room that the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

In some embodiments, a gantry system with a helical delivery may be used to rotate the imaging system 1210. For example, the gantry system may be used to acquire two, three, or more images (e.g., x-ray images) at different angles. The radiation treatment delivery system may also include a rotational imaging system 109 that is positioned around the patient.

In one implementation, the system 1200 includes a frameless robotic radiosurgery system (e.g., CyberKnife® treatment delivery system). In another implementation, the system 1200 is coupled to a gantry-based LINAC treatment system where, for example, LINAC 1201 is coupled to a gantry of a gantry based system. Alternatively, system 1200 may be used with other types of radiation treatment systems, for example, a helical delivery system as discussed below.

Figure 1B:
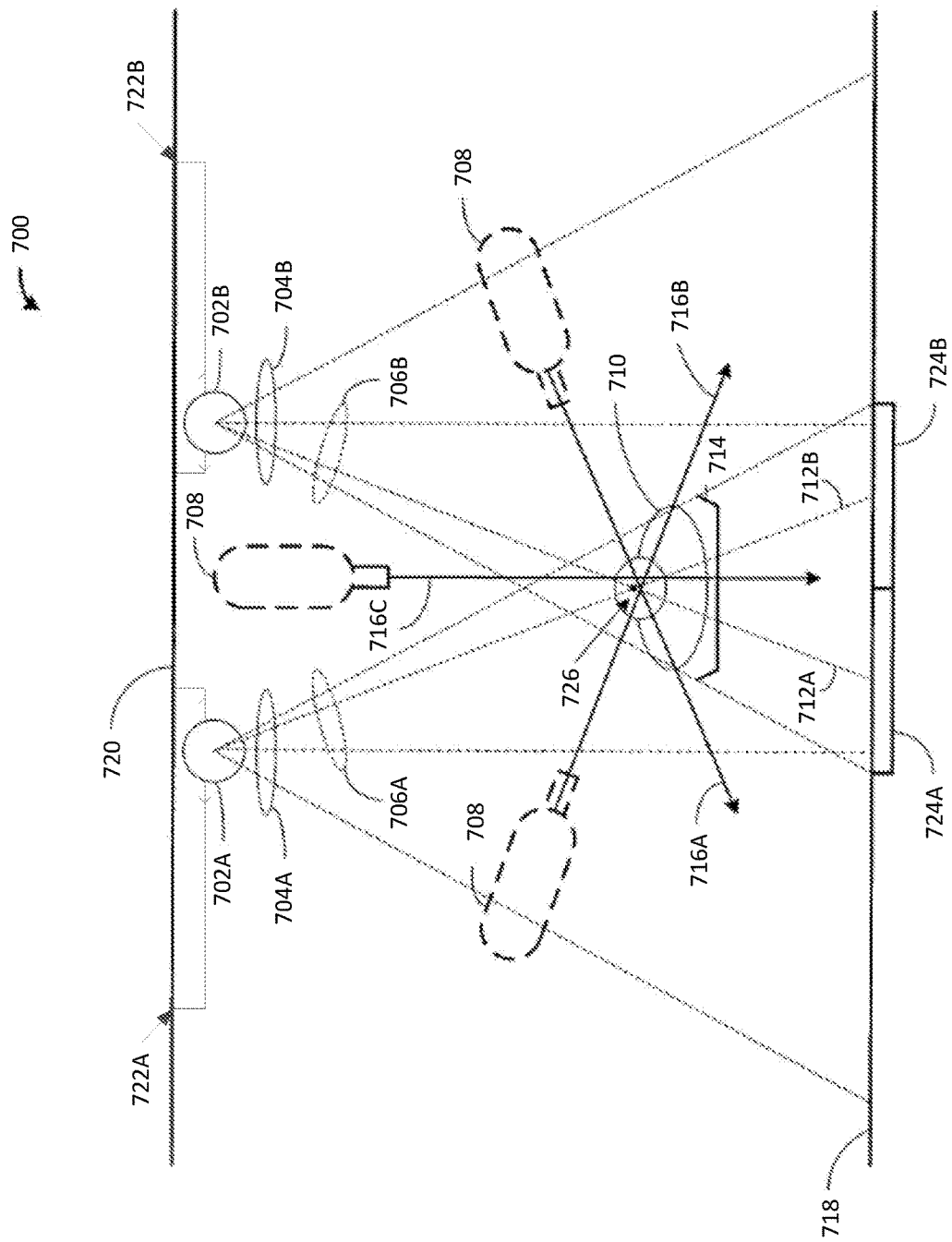
FIG. 1B is a cross-section of the radiation treatment system in accordance with embodiments described herein.

FIG. 1B illustrates the configuration of an image-guided radiation treatment (IGRT) system 700. In general, the IGRT system 700 may correspond to the radiation treatment system 1200 of FIG. 1A.

As shown in FIG. 1B, the IGRT system 700 may include to kilovoltage (kV) imaging sources 702A and 702B that may be mounted on tracks 722A and 722B on the ceiling 720 of an operating room and may be aligned to project imaging x-ray beams 704A and 704B from two different positions such that a ray 712A of beam 704A intersects with a ray 712B of beam 704B at an imaging center 726 (i.e., isocenter), which provides a reference point for positioning the LINAC 708 to generate treatment beams 716A, 716B and 716C and the patient 710 on treatment couch 714 during treatment. After passing through the patient 710, imaging x-ray beams 704A and 704B may illuminate respective imaging surfaces of x-ray detectors 724A and 724B, which may be mounted at or near the floor 718 of the operating room and substantially parallel to each other (e.g., within 5 degrees). The kV imaging sources 702A and 702B may be substantially coplanar such that the imaging surfaces of kV imaging sources 702A and 702B form a single imaging plane. In one embodiment, kV imaging sources 702A and 702B may be replaced with a single kV imaging source. Once an x-ray image of the patient 710 has been generated, the LINAC 708 may rotate to generate a treatment beam 716 from a different angle. While the LINAC 708 rotates to the different angle, the kV imaging sources 702A and 702B may move along tracks 722A and 722B to generate x-ray images of the patient 710 from a new angle.

Figure 2:
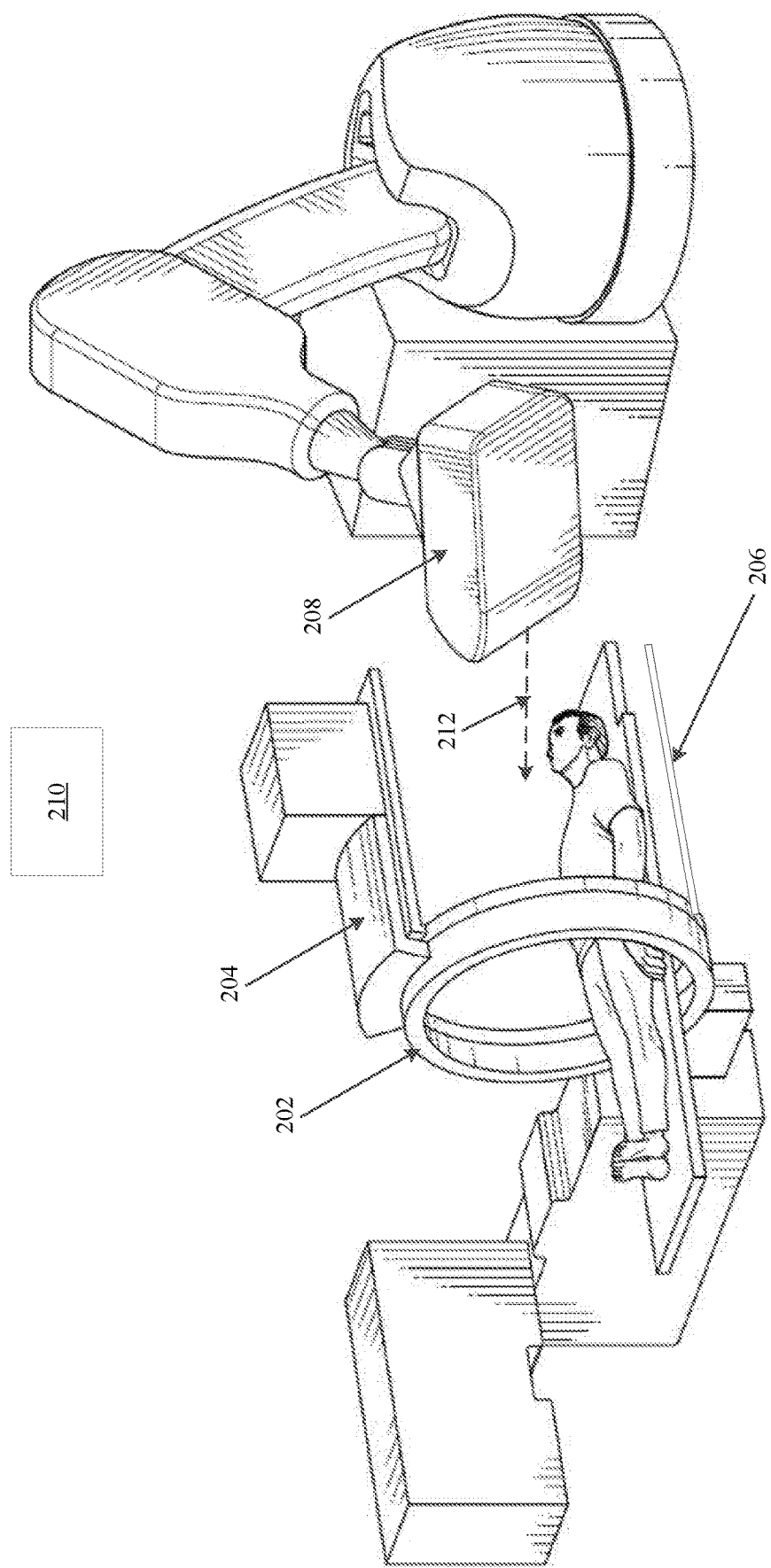
FIG. 2 illustrates a volumetric imaging device in an extended position, in accordance with embodiments described herein.

FIG. 2 illustrates a volumetric imaging device 202 in an extended position, in accordance with embodiments described herein. In one embodiment, the volumetric imaging device includes a source 204 and a detector 206. In one embodiment, the source 204 and detector 206 of the volumetric imager 202 may be used during radiation treatment to track a target and align a patient. In one embodiment, the volumetric imaging device 202 may be uses to take a series of images, which may be used to perform the tracking and aligning. In another embodiment, the volumetric imaging device 202 may be used in combination with a second imager, such as a static 2D x-ray imager (e.g., 210), to perform the tracking and aligning. In one embodiment, when the volumetric imaging device 202 is in an extended position, there is potential to collide with a radiation treatment device (e.g., LINAC 208) and/or a treatment beam 212 of a radiotherapy device. While in an extended position, the source 204 and detector 206 of the volumetric imaging device 202 may maintain an orthogonal alignment to the LINAC 208 and/or treatment beam 212, so as to avoid such collisions. Addition details regarding maintaining the orthogonal alignment are provided with respect to FIGS. 3, 5A, and 5B.

Figure 3:
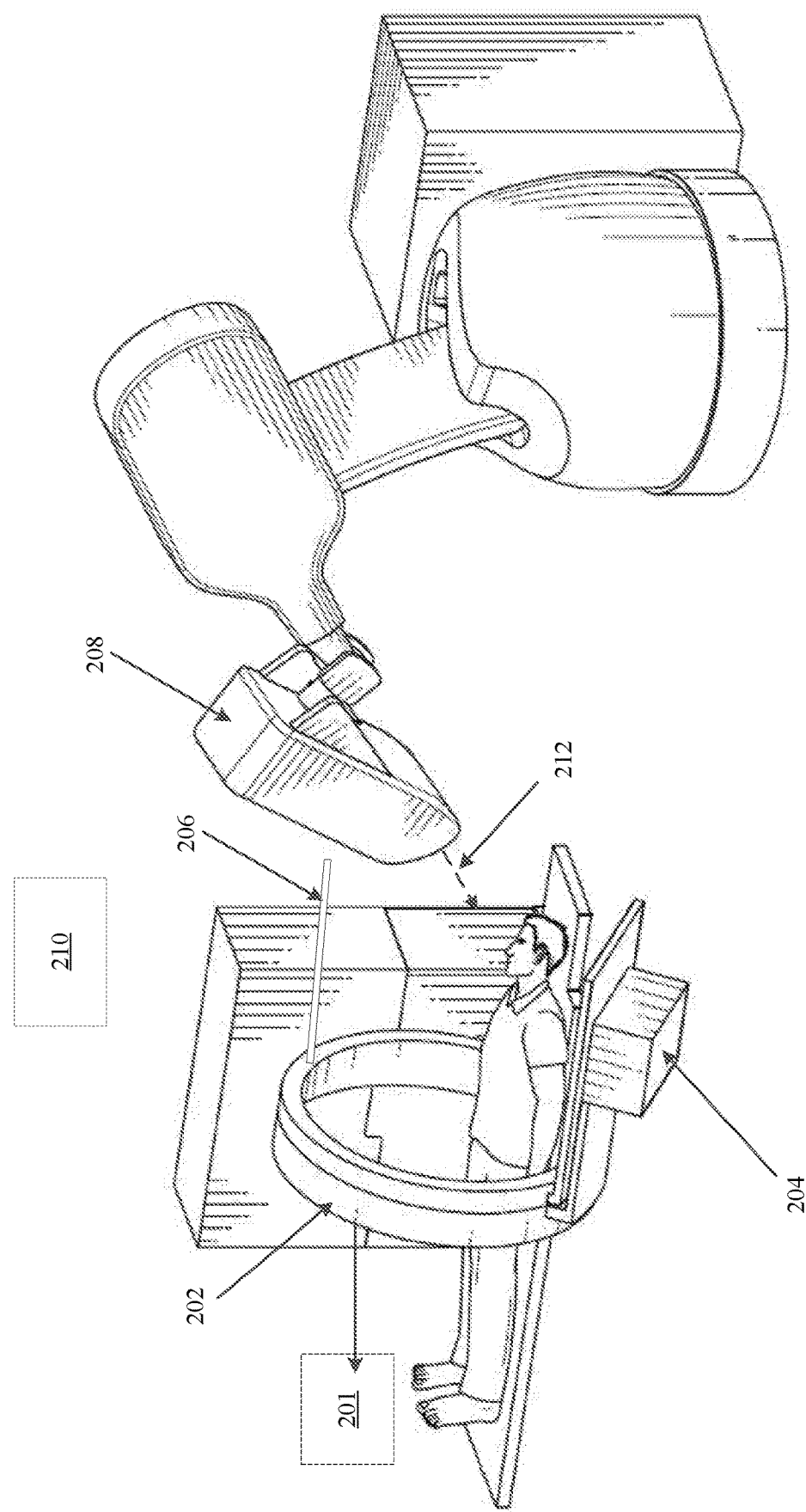
FIG. 3 illustrates a volumetric imaging device in a retracted position, in accordance with embodiments described herein.

FIG. 3 illustrates a volumetric imaging device 202 in a retracted position, in accordance with embodiments described herein. In one embodiment, the volumetric imaging device includes a source 204 and a detector 206. In one embodiment, the source 204 and detector 206 of the volumetric imager 202 may be used during radiation treatment to track a target and align a patient. In one embodiment, the volumetric imaging device 202 may be uses to take a series of images, which may be used to perform the tracking and aligning. In another embodiment, the volumetric imaging device 202 may be used in combination with a second imager, such as a static 2D x-ray imager (e.g., 210), to perform the tracking and aligning. The volumetric imaging device 202 may alternate between the retracted position, when a treatment beam is active, and an extended position, when the treatment beam is inactive. When in the extended position, the volumetric imager 202 may perform the tracking an aligning. In one embodiment, when the volumetric imaging device 202 is in a retracted position, the source 204 and detector 206 of the volumetric imaging device 202 may maintain an orthogonal alignment to the LINAC 208 and/or treatment beam 212, so as to avoid such collisions when the volumetric imager 202 is moved to the extended position. Advantageously, maintain the orthogonal alignment while the volumetric imaging device 202 is in the retracted position allows for relatively little time to be added to treatment time. Addition details regarding maintaining the orthogonal alignment are provided with respect to FIGS. 5A, and 5B.

Figure 4:
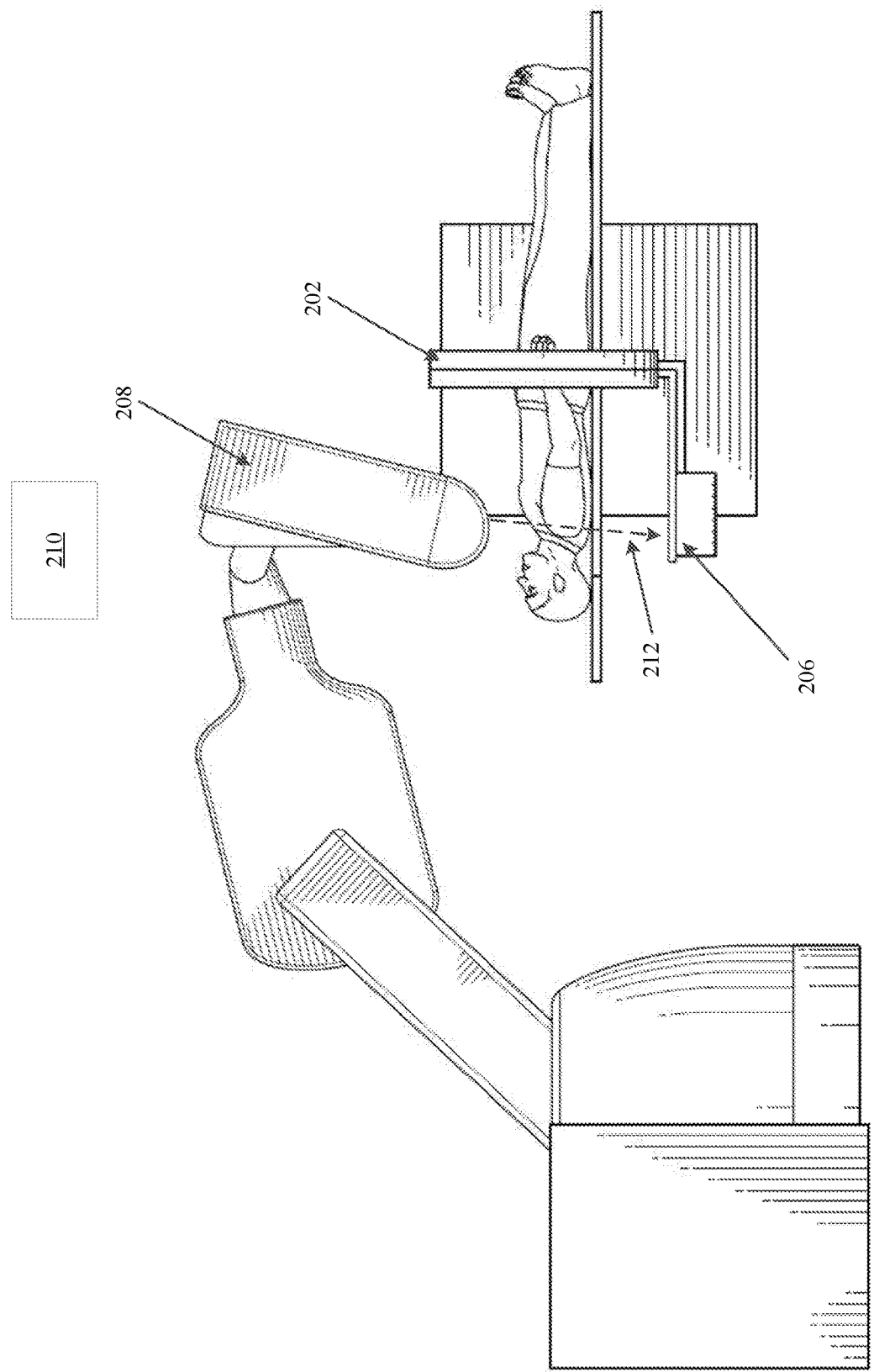
FIG. 4 illustrates a volumetric imaging device in position for MV Portal Imaging, in accordance with embodiments described herein.

FIG. 4 illustrates a volumetric imaging device 202 in position for MV Portal Imaging, in accordance with embodiments described herein. In one embodiment, the volumetric imaging device includes a source 204 and a detector 206. In one embodiment, the source 204 and detector 206 of the volumetric imager 202 may be used during radiation treatment to track a target and align a patient. In one embodiment, for MV Portal Imaging, only the detector 206 is used to perform the tracking and aligning. During MV Portal Imaging, detector 206 may be put in a position to allow the capturing of a treatment beam 212 of a LINAC 208 after it passes through a patient.

In one embodiment, the volumetric imaging device 202 may be uses to take a series of MV Portal images, which may be used to perform the tracking and aligning. In another embodiment, the volumetric imaging device 202 may be used in combination with a second imager, such as a static 2D x-ray imager (e.g., 210), to perform the tracking and aligning. The detector 206 of the volumetric imaging device 202 may be moved into a position that allows direct alignment with the treatment beam 212, while the source 204 is moved to a position that avoids collisions with the LINAC 208 and the treatment beam 212. Addition details regarding maintaining the direct alignment are provided with respect to FIGS. 5A, and 5B.

Figure 5A:
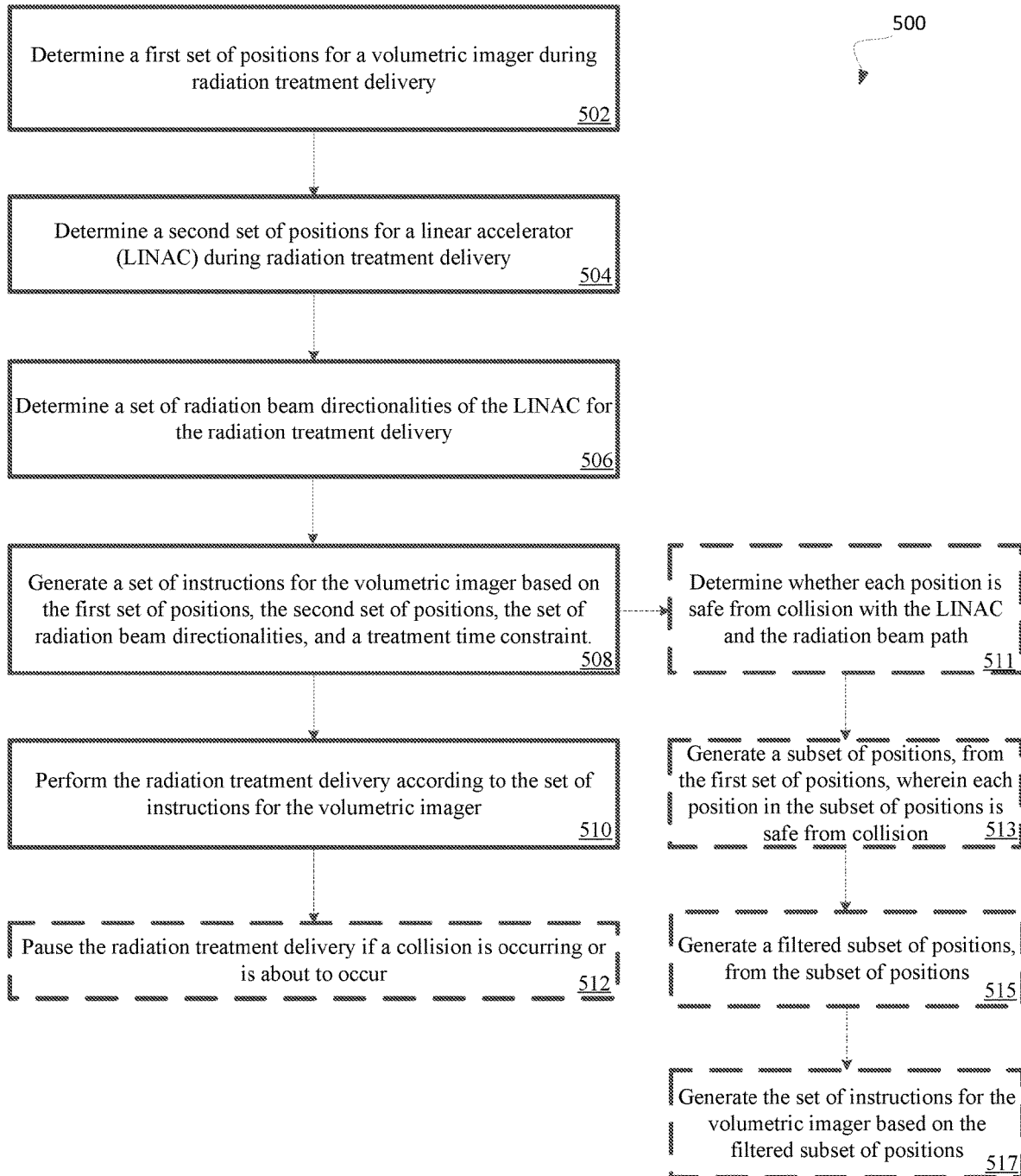
FIG. 5A illustrates a method of coordinated motion of a rotating 2D x-ray imager and a robotic therapy device, in accordance with embodiments described herein.

FIG. 5A illustrates a first method 500 of coordinated motion of a rotating 2D x-ray imager and a robotic therapy device, in accordance with embodiments described herein. In general, the method 500 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 500 may be performed by processing logic of the radiation treatment system 1200 of FIG. 1.

As shown in FIG. 5A, the method 500 may begin at block 502 with the processing logic determining a first set of positions for a volumetric imager during radiation treatment delivery. In one embodiment, the first set of positions corresponds to possible volumetric imager positions for the radiation treatment delivery. In one embodiment, during treatment planning, processing logic determines a complete set of possible positions for the volumetric imager during treatment. In another embodiment, processing logic determines the positions during treatment planning.

At block 504, processing logic determines a second set of positions for a linear accelerator (LINAC) during radiation treatment delivery. In one embodiment, the second set of positions corresponds to determined LINAC positions for the radiation treatment delivery. In one embodiment, during treatment planning, processing logic determines a complete set of possible positions for the LINAC during treatment. In another embodiment, processing logic determines the positions during treatment planning.

At block 506, processing logic determines a set of radiation beam directionalities of the LINAC for the radiation treatment delivery. In one embodiment, for each of the second set of positions for the LINAC, a radiation beam corresponds to a radiation beam directionality from a set of possible radiation beam directionalities. In one embodiment, during treatment planning, processing logic determines a complete set of possible directionalities for the treatment beam of the LINAC during treatment. In another embodiment, processing logic determines the directionalities during treatment planning.

At block 508, processing logic generates a set of instructions for the volumetric imager based on the first set of positions, the second set of positions, the set of radiation beam directionalities, and a treatment time constraint. Processing logic may also generate the set of instructions for the volumetric imager based on a radiation beam size during radiation treatment delivery. In another embodiment, a maximum possible beam size, instead of an actual beam size, is utilized to generate the instructions. In one embodiment, the set of instructions is generated to avoid a collision between the volumetric imager and the LINAC during treatment. In another embodiment, the set of instructions is generated to avoid a collision between the volumetric imager and the radiation beam during treatment. In another embodiment, the set of instructions is generated to avoid a collision between the volumetric imager and the LINAC and between the volumetric imager and the radiation beam during treatment. The set of instructions may include physical locations of the volumetric imager and timing values corresponding to the physical locations.

In one embodiment, at block 511, to generate the instructions, processing logic may determine whether each position in the first set of positions is safe from collision with the LINAC and/or from collision with the radiation beam path, along which the LINAC is to direct the radiation beam. Processing logic at block 513 generates a subset of positions, from the first set of positions, wherein each position in the subset of positions is safe from collision. At block 515, processing logic generates a filtered subset of positions, from the subset of positions. The filtered subset may include positions of the subset of positions that do not violate the treatment time constraint. At block 517, processing logic generates the set of instructions for the volumetric imager based on the filtered subset of positions. Advantageously, by generating the set of instructions from the filtered subset of position, the resulting treatment may avoid collisions while adding not more than a threshold time to the total treatment time.

Instructions may be generated to optimize various treatment characteristics. For example, in one embodiment, the instructions may optimize volumetric imager movement based on a minimum motion time of the radiation treatment delivery. In another embodiment, the instructions may optimize volumetric imager movement based on minimum volumetric imager movement during radiation treatment delivery. In yet another embodiment, the instructions may optimize volumetric imager movement based on maximizing a distance between the radiation beam and the volumetric imager during delivery. In various other embodiments, other optimizations may be made.

At block 510, processing logic operate the volumetric imager during the radiation treatment delivery according to the set of instructions. In one embodiment, processing logic performs the radiation treatment delivery. Optionally, processing logic may, during treatment, determine whether a collision is occurring or is about to occur and, at block 512, pause the radiation treatment delivery in response to the collision occurring or about to occur. Advantageously, by performing this secondary check, collisions and the harm caused by them may be reduced and/or completely eliminated.

Processing logic may perform a simulated radiation treatment delivery based on the set of instructions for the volumetric imager and providing a notification to a user in response to a collision occurring during the simulated delivery. In one embodiment, processing logic may perform the simulated radiation treatment delivery and provide the notification based on at least one of a change in a couch position or a change in imaging corrections. By performing a simulated radiation treatment delivery, potential collisions may be detected before collisions actually occur during a live treatment.

Figure 5B:
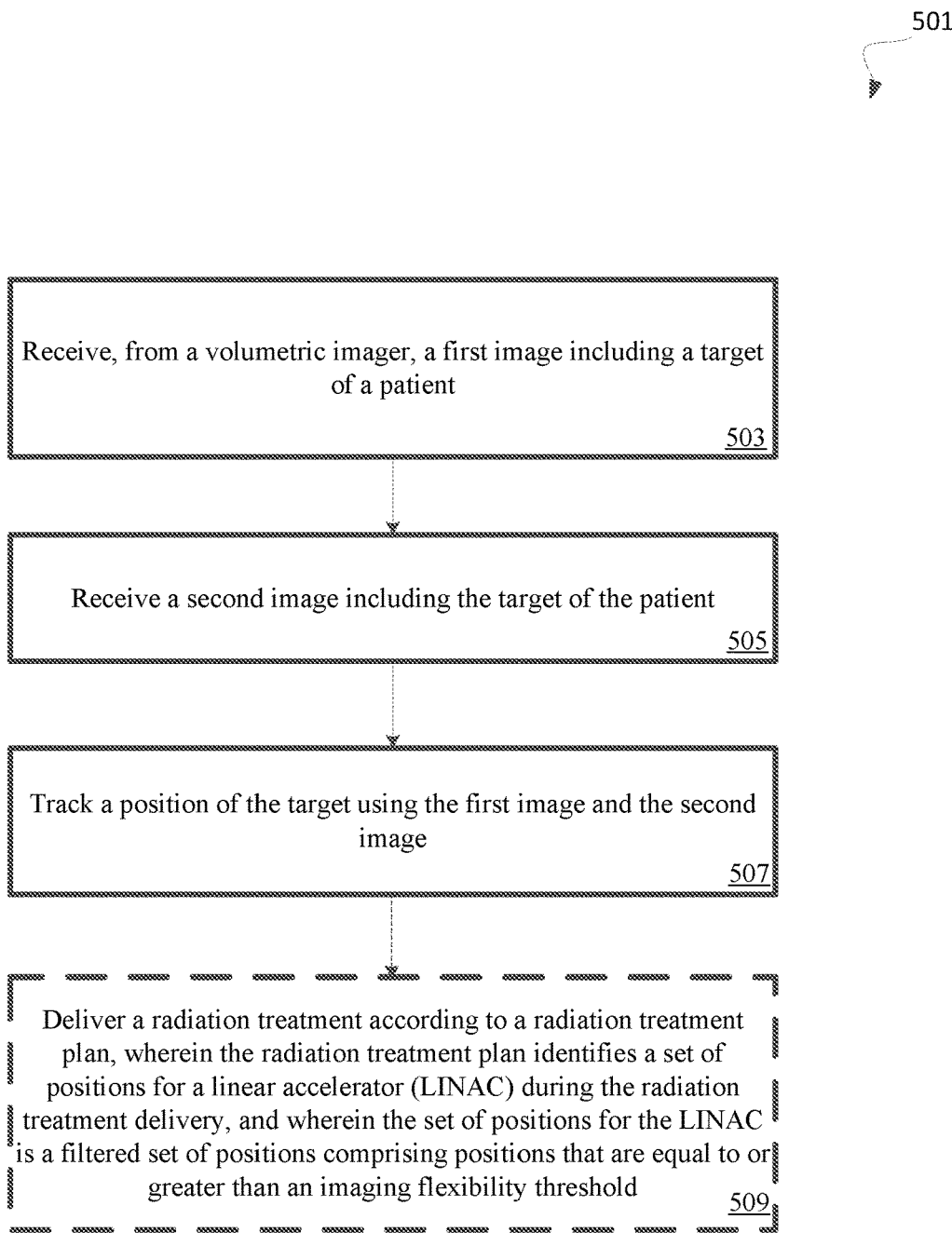
FIG. 5B illustrates a first method of using a volumetric imager to perform target tracking, in accordance with embodiments described herein.

FIG. 5B illustrates a first method 501 of using a volumetric imager to perform target tracking, in accordance with embodiments described herein. In general, the method 501 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 501 may be performed by processing logic of the radiation treatment system 1200 of FIG. 1.

At block 503, processing logic begins by receiving, from a volumetric imager, a first image including a target of a patient, and, at block 505, processing logic receives a second image including the target of the patient. In one embodiment, the first image is a three-dimensional (3D) intrafraction image. The 3D intrafraction image may be one of: a kilovoltage cone beam computed tomography (kV-CBCT) image, a megavoltage cone beam computed tomography (MV-CBCT) image, a megavoltage computed tomography (MVCT) image, or any other image type. In one embodiment, the second image is received from the volumetric imager. In another embodiment, the second image is received from a static x-ray imager.

Processing logic at block 507 tracks a position of the target using the first image and the second image. In one embodiment, to perform the tracking, processing logic maintains an orthogonal alignment between a treatment beam of a linear accelerator (LINAC) and a source and detector pair of the volumetric imager during a radiation treatment. Advantageously, by maintaining the orthogonal alignment collisions between the LINAC (and the treatment beam of the LINAC) and the volumetric imager may be prevented. Optionally, at block 509, processing logic may deliver a radiation treatment according to a radiation treatment plan, wherein the radiation treatment plan identifies a set of positions for a linear accelerator (LINAC) during the radiation treatment delivery. The set of positions for the LINAC may be a filtered set of positions including positions that are equal to or greater than an imaging flexibility threshold, as described herein.

Figure 5C:
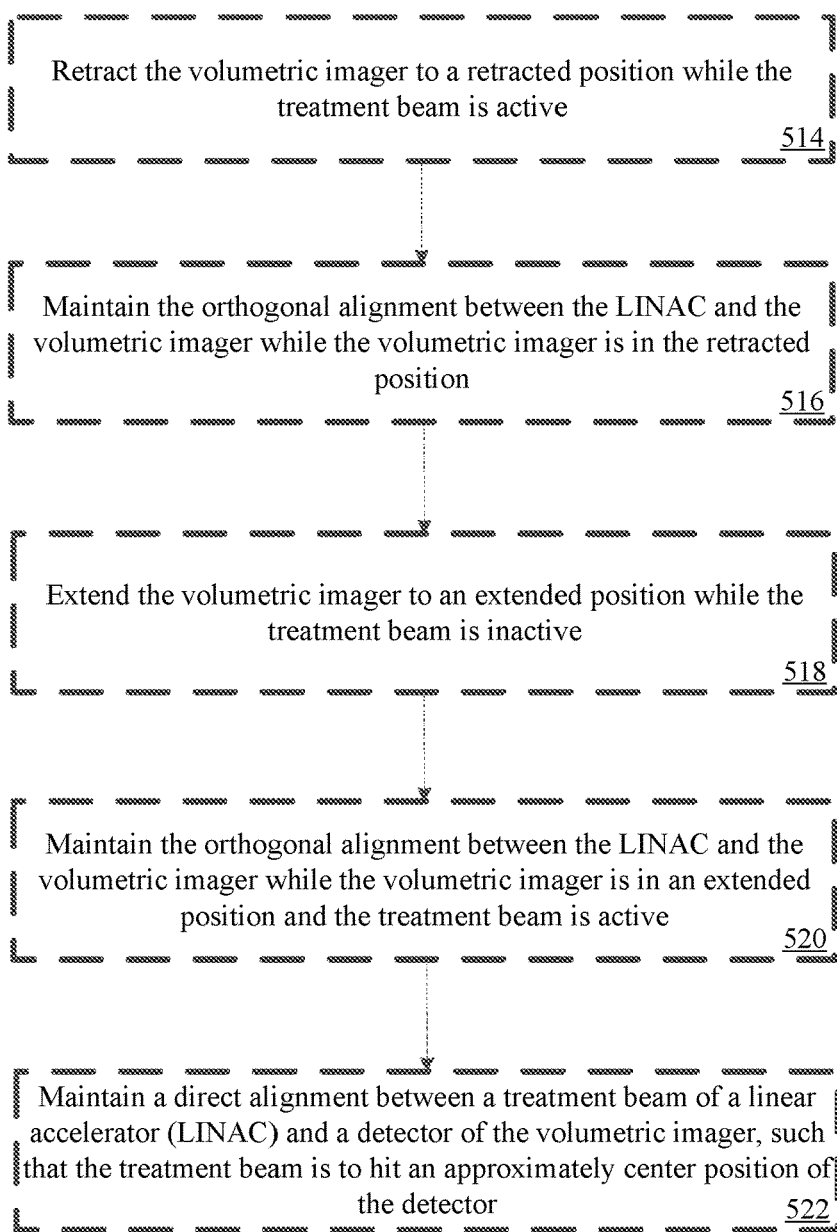
FIG. 5C illustrates a second method of using a volumetric imager to perform target tracking.

FIG. 5C illustrates a second method 519 of using a volumetric imager to perform target tracking, in accordance with embodiments described herein. In general, the method 519 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 519 may be performed by processing logic of the radiation treatment system 1200 of FIG. 1.

At block 514, processing logic begins by retracting the volumetric imager to a retracted position while the treatment beam is active. At block 516, processing logic maintains the orthogonal alignment between the LINAC and the volumetric imager while the volumetric imager is in the retracted position, and, at block 518, processing logic extends the volumetric imager to an extended position while the treatment beam is inactive.

At block 520, which may be performed instead of or in addition to the operations of blocks 514-518, processing logic maintains the orthogonal alignment between the LINAC and the volumetric imager while the volumetric imager is in an extended position and the treatment beam is active. At block 522, processing logic maintains a direct alignment between a treatment beam of a linear accelerator (LINAC) and a detector of the volumetric imager. In this embodiment, the treatment beam is to hit an approximately center position of the detector to perform MV Portal Imaging. In this embodiment, the first image is an MV Portal image.

In one embodiment, the volumetric imager of method 519 includes a source and a detector, as described herein, and processing logic is further to modify a position of the source of the volumetric imager to avoid a collision between the volumetric imager and the LINAC during treatment. In another embodiment, the processing logic is to avoid a collision between the volumetric imager and the radiation beam during treatment. In another embodiment, the processing logic is to avoid a collision between the volumetric imager and the LINAC and between the volumetric imager and the radiation beam during treatment.

It should be noted that the embodiments described herein can be used with various types of planning image types, including diagnostic kV-CT, MRI, kV-CBCT, and MVCT. The methods discussed herein may be used with MR-based planning (e.g., in the case where no CT is used or available for treatment planning). The embodiments discussed herein can also be used with various types of intrafraction 3D images, including kV-CBCT, MVCT, MVCBCT, and in-room helical/diagnostic kV-CT. The embodiments discussed herein can be used with various types of intrafraction 2D imaging systems, including stereo x-ray pair, a rotating monoscopic 2D x-ray imager, and C-arm intraoperative imaging systems (used in surgical and interventional guidance applications). Although the embodiments are described at times in relation to a robotic surgery system, in alternative embodiments, the method discussed herein may be used with other types of treatment delivery systems such as a helical delivery system and gantry-based systems. In addition, although the embodiments are described at times in relation to the medPhoton ImagingRing System (IRS), in alternative embodiments, the methods may be used with other types of volumetric imaging systems.

Figure 6:
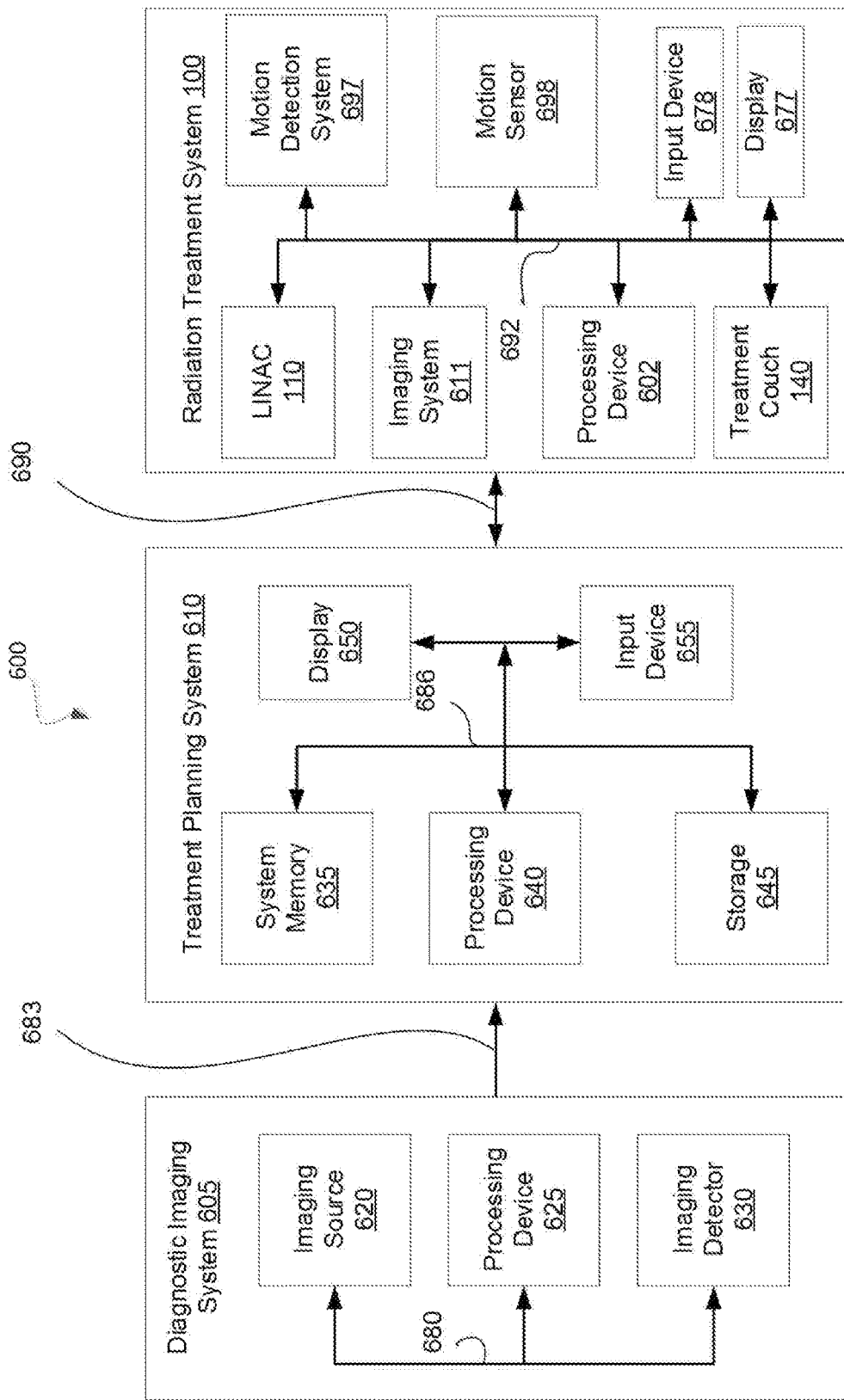
FIG. 6 illustrates examples of different systems that may be used in the generating of the performing of radiation treatment, in accordance with embodiments described herein.

FIG. 6 illustrates examples of different systems 600 within which a set of instructions, for causing the systems to perform any one or more of the methodologies discussed herein, may be executed. In alternative implementations, the machine may be connected (e.g., networked) to other machines in a LAN, an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example radiation treatment delivery system 110, which may represent treatment delivery systems 1200, 800, 709, or some other system, includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 630.

Processing device 602 represents one or more general-purpose processing devices such as a microprocessor, a central processing unit, or the like. Processing device may be the same or a different processing device as processing device 1230 and may also represent the processing device in treatment delivery workstation 150. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computer system 600 may further include a network interface device 608 to communicate over the network 620. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), a graphics processing unit 622, a signal generation device 616 (e.g., a speaker), graphics processing unit 622, video processing unit 628, and audio processing unit 632.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include an x-ray motion component 699 to implement functionality corresponding to the disclosure herein. While the machine-readable storage medium 624 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 7:
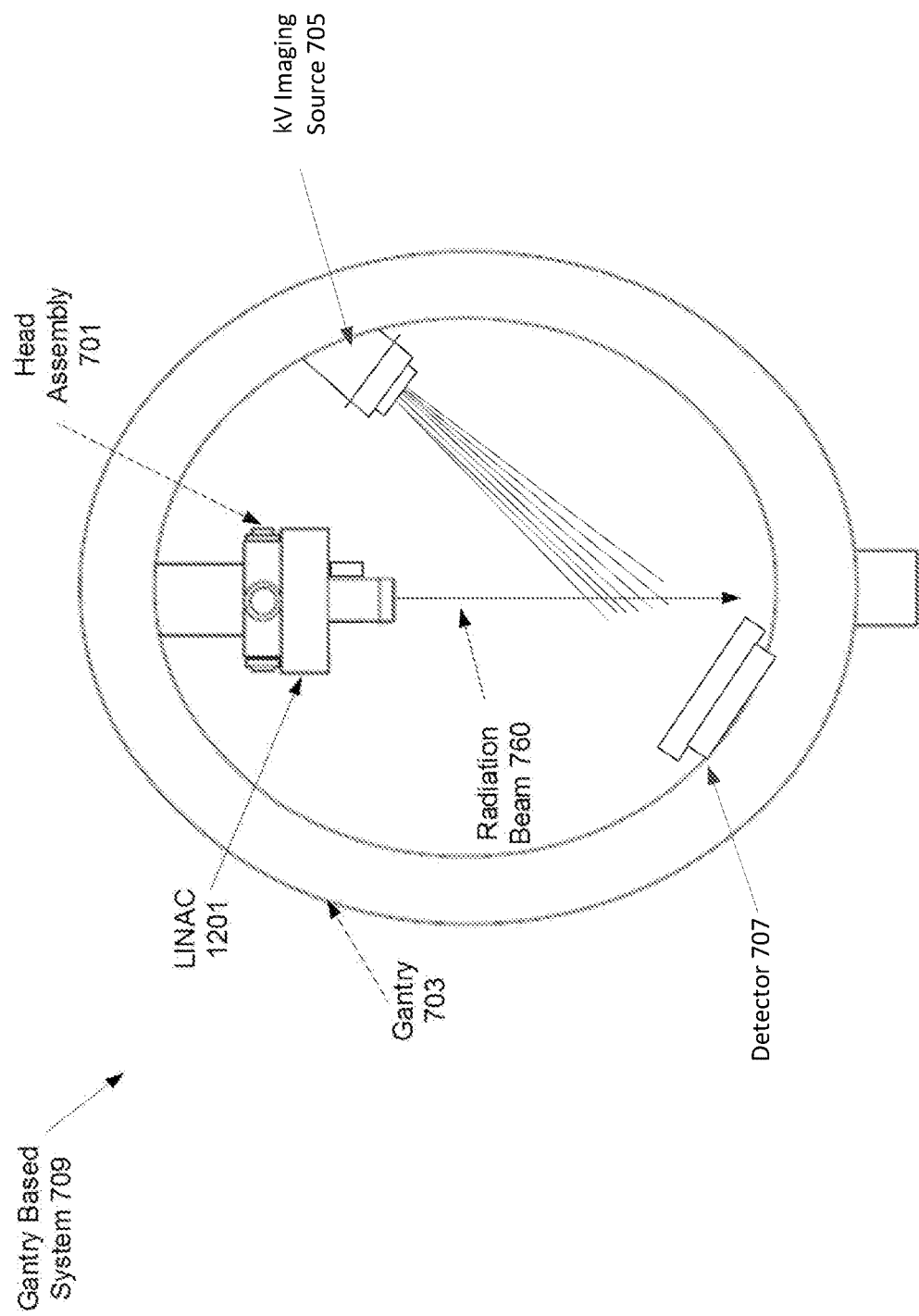
FIG. 7 illustrates a gantry based intensity modulated radiation treatment system, in accordance with embodiments described herein.

FIG. 7 illustrates a gantry based intensity modulated radiation treatment (IMRT) system 709, in accordance with implementations of the present disclosure. In gantry based system 709, a radiation source (e.g., a LINAC 1201) having a head assembly 701 is mounted on a gantry 703. In one embodiment, radiation beams 160 may be delivered from several positions on a circular plane of rotation (e.g., around an axis of rotation). In one embodiment, system 709 includes a treatment imaging system, which may include a kV imaging source 705 and an x-ray detector 707. The kV imaging source 705 may be used to generate x-ray images of a ROI of patient by directing a sequence of x-ray beams at the ROI which are incident on the x-ray detector 707 opposite the kV imaging source 705 to image the patient for setup and generate in-treatment images. The resulting system generates arbitrarily shaped radiation beams 760 that intersect each other at an isocenter to deliver a dose distribution to the target location. In one implementation, the gantry based system 700 may be a c-arm based system.

Figure 8:
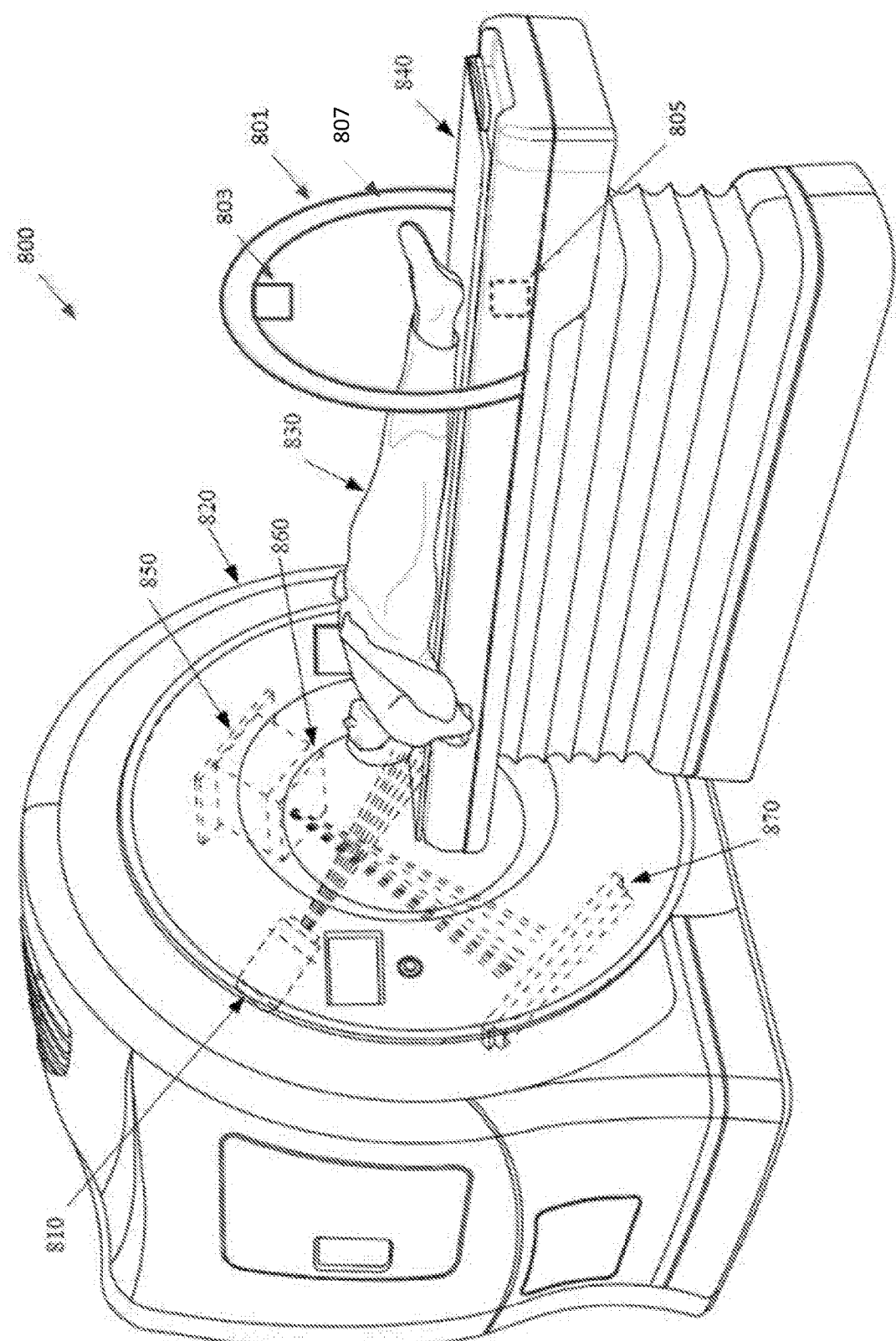
FIG. 8 illustrates a helical radiation delivery system, in accordance with embodiments described herein.

FIG. 8 illustrates a helical radiation delivery system 800 in accordance with embodiments of the present disclosure. The helical radiation delivery system 800 may include a linear accelerator (LINAC) 810 mounted to a ring gantry 820. The LINAC 810 may be used to generate a narrow intensity modulated pencil beam (i.e., treatment beam) by directing an electron beam towards an x-ray emitting target. The treatment beam may deliver radiation to a target region (i.e., a tumor). The ring gantry 820 generally has a toroidal shape in which the patient 830 extends through a bore of the ring/toroid and the LINAC 810 is mounted on the perimeter of the ring and rotates about the axis passing through the center to irradiate a target region with beams delivered from one or more angles around the patient. During treatment, the patient 830 may be simultaneously moved through the bore of the gantry on treatment couch 840.

The helical radiation delivery system 800 includes a treatment imaging system, which may include a kV imaging source 850 and an x-ray detector 870. The kV imaging source 850 may be used to generate x-ray images of a region of interest (ROI) of patient 830 by directing a sequence of x-ray beams at the ROI which are incident on the x-ray detector 870 opposite the kV imaging source 850 to image the patient 830 for setup and generate in-treatment images. The treatment imaging system may further include a collimator 860. In one embodiment, the collimator 860 may be a variable aperture collimator. In another embodiment, the collimator 860 may be a multi-leaf collimator (MLC). The MLC includes a housing that houses multiple leaves that are movable to adjust an aperture of the MLC to enable shaping of an imaging x-ray beam. In another embodiment, the variable aperture collimator 860 may be an iris collimator containing trapezoidal blocks that move along a frame in a manner similar to a camera iris to produce an aperture of variable size that enables shaping of the imaging x-ray beam. The kV imaging source 850 and the x-ray detector 870 may be mounted orthogonally relative to the LINAC 810 (e.g., separated by 90 degrees) on the ring gantry 820 and may be aligned to project an imaging x-ray beam at a target region and to illuminate an imaging plane of detector 870 after passing through the patient 130. In some embodiments, the LINAC 810 and/or the kV imaging source 850 may be mounted to a C-arm gantry in a cantilever-like manner, which rotates the LINAC 810 and kV imaging source 850 about the axis passing through the isocenter. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Helical radiation delivery system 800 includes also includes a secondary imaging system 801. Imaging system 801 is a CBCT imaging system, for example, the medPhoton ImagingRing System. Alternatively, other types of volumetric imaging systems may be used. The secondary imaging system 801 includes a rotatable gantry 807 (e.g., a ring) attached to an arm and rail system (not shown) that move the rotatable gantry 807 along one or more axes (e.g., along an axis that extends from a head to a foot of the treatment couch 840. An imaging source 803 and a detector 805 are mounted to the rotatable gantry 807. The rotatable gantry 807 may rotate 360 degrees about the axis that extends from the head to the foot of the treatment couch. Accordingly, the imaging source 803 and detector 805 may be positioned at numerous different angles. In one embodiment, the imaging source 803 is an x-ray source and the detector 805 is an x-ray detector. In one embodiment, the secondary imaging system 801 includes two rings that are separately rotatable. The imaging source 803 may be mounted to a first ring and the detector 805 may be mounted to a second ring.

It will be apparent from the foregoing description that aspects of the present disclosure may be embodied, at least in part, in software. That is, the techniques may be carried out in a computer system or other data processing system in response to a processing device 625, 640, or 602 (see FIG. 6), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 602.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method of operating a radiation treatment delivery system, comprising:
   determining a first set of possible positions for a component of a volumetric imager for radiation treatment delivery, the first set of positions corresponding to possible volumetric imager positions for the radiation treatment delivery;
   determining a second set of positions for a linear accelerator (LINAC) for radiation treatment delivery, the second set of positions corresponding to determined LINAC positions for the radiation treatment delivery;
   determining a set of radiation beam directionalities of the LINAC for the radiation treatment delivery, wherein for each of the second set of positions for the LINAC a radiation beam corresponds to a radiation beam directionality from a plurality of possible radiation beam directionalities;
   generating, by a processing device, a set of instructions for the volumetric imager based on the first set of positions, the second set of positions, the set of radiation beam directionalities, and a treatment time constraint to avoid a collision between the volumetric imager and the LINAC and between the volumetric imager and the radiation beam, wherein the set of instructions comprises physical locations of the volumetric imager and timing values corresponding to the physical locations; and operating the volumetric imager during the radiation treatment delivery according to the set of instructions.

2. The method of claim 1, wherein generating the set of instructions for the volumetric imager comprises:
determining whether each position in the first set of positions is safe from collision with the LINAC and from collision with the radiation beam path, along which the LINAC is directing the radiation beam;
generating a subset of positions, from the first set of positions, wherein each position in the subset of positions is safe from collision;
generating a filtered subset of positions, from the subset of positions, wherein the filtered subset comprises positions of the subset of positions that do not violate the treatment time constraint; and
generating the set of instructions for the volumetric imager based on the filtered subset of positions.

3. The method of claim 1, further comprising: optimizing the set of instructions for the volumetric imager based on a minimum motion time of the radiation treatment delivery.

4. The method of claim 1, further comprising: optimizing the set of instructions for the volumetric imager based on minimum volumetric imager movement during radiation treatment delivery.

5. The method of claim 1, further comprising: optimizing the set of instructions for the volumetric imager based on maximizing a distance between the radiation beam and the volumetric imager during delivery.

6. The method of claim 1, further comprising: generating the set of instructions for the volumetric imager based on a radiation beam size during radiation treatment delivery.

7. The method of claim 1, further comprising:
determining whether a collision is occurring or is about to occur; and
pausing the radiation treatment delivery in response to the collision occurring or about to occur.

8. The method of claim 1, further comprising:
performing a simulated radiation treatment delivery based on the set of instructions for the volumetric imager; and
providing a notification to a user in response to a collision occurring during the simulated delivery.

9. A radiation treatment delivery system comprising:
a memory; and
a processing device, operatively coupled with the memory, to:
determine a first set of possible positions for a component of a volumetric imager for radiation treatment delivery, the first set of positions corresponding to possible volumetric imager positions for the radiation treatment delivery;
determine a second set of positions for an x-ray linear accelerator (LINAC) for radiation treatment delivery, the second set of positions corresponding to predetermined LINAC positions for the radiation treatment delivery;
determine a third set of positions for a radiation beam of the LINAC during radiation treatment delivery, the third set of positions corresponding to predetermined radiation beam positions for the radiation treatment delivery;
generate, by the processing device, a set of instructions for the volumetric imager based on the first set of positions, the second set of positions, the third set of radiation beam positions, and a treatment time constraint to avoid a collision between the volumetric imager and the LINAC and between the volumetric imager and the radiation beam, wherein the set of instructions comprises physical locations of the volumetric imager and timing values corresponding to the physical locations; and
operate the volumetric imager during the radiation treatment delivery according to the set of instructions.

10. The radiation treatment delivery system of claim 9, wherein to generate the set of instructions for the volumetric imager, the processing device is to:
determine whether each position in the first set of positions is safe from collision with the LINAC and from collision with the radiation beam path, along which the LINAC is directing the radiation beam;
generate a subset of positions, from the first set of positions, wherein each position in the subset of positions is safe from collision;
generate a filtered subset of positions, from the subset of positions, wherein the filtered subset comprises positions of the subset of positions that do not violate the treatment time constraint; and
generate the set of instructions for the volumetric imager based on the filtered subset of positions.

11. The radiation treatment delivery system of claim 9, the processing device further to: optimize the set of instructions for the volumetric imager based on a minimum motion time of the radiation treatment delivery.

12. The radiation treatment delivery system of claim 9, the processing device further to: optimize the set of instructions for the volumetric imager based on minimum volumetric imager movement during radiation treatment delivery.

13. The radiation treatment delivery system of claim 9, the processing device further to: optimize the set of instructions for the volumetric imager based on maximizing a distance between the radiation beam and the volumetric imager during delivery.

14. The radiation treatment delivery system of claim 9, the processing device further to: generate the set of instructions for the volumetric imager based on a radiation beam size during radiation treatment delivery.

15. The radiation treatment delivery system of claim 9, the processing device further to:
determine whether a collision is occurring or is about to occur; and
pause the radiation treatment delivery in response to the collision occurring or about to occur.

16. The radiation treatment delivery system of claim 9, the processing device further to:
perform a simulated radiation treatment delivery based on the set of instructions for the volumetric imager; and
provide a notification to a user in response to a collision occurring during the simulated delivery.

17. A non-transitory computer readable medium comprising instructions that, when executed by a processing device of a radiation treatment delivery system, cause the processing device to:
determine a first set of possible positions for a component of a volumetric imager for radiation treatment delivery, the first set of positions corresponding to possible volumetric imager positions for the radiation treatment delivery;
determine a second set of positions for an x-ray linear accelerator (LINAC) for radiation treatment delivery, the second set of positions corresponding to predetermined LINAC positions for the radiation treatment delivery;

determine a third set of positions for a radiation beam of the LINAC during radiation treatment delivery, the third set of positions corresponding to predetermined radiation beam positions for the radiation treatment delivery;

generate, by the processing device, a set of instructions for the volumetric imager based on the first set of positions, the second set of positions, the third set of positions, and a treatment time constraint to avoid a collision between the volumetric imager and the LINAC and between the volumetric imager and the radiation beam, wherein the set of instructions comprises physical locations of the volumetric imager and timing values corresponding to the physical locations; and operate the volumetric imager during the radiation treatment delivery according to the set of instructions.

18. The non-transitory computer readable medium of claim 17, wherein to generate the set of instructions for the volumetric imager, the processing device is to:

determine whether each position in the first set of positions is safe from collision with the LINAC and from collision with the radiation beam path, along which the LINAC is directing the radiation beam;

generate a subset of positions, from the first set of positions, wherein each position in the subset of positions is safe from collision;

generate a filtered subset of positions, from the subset of positions, wherein the filtered subset comprises positions of the subset of positions that do not violate the treatment time constraint; and generate the set of instructions for the volumetric imager based on the filtered subset of positions.

19. The non-transitory computer readable medium of claim 17, the processing device further to: optimize the set of instructions for the volumetric imager based on at least one of: a minimum motion time of the radiation treatment delivery, minimum volumetric imager movement during radiation treatment delivery, or maximizing a distance between the radiation beam and the volumetric imager during delivery.

20. The non-transitory computer readable medium of claim 17, the processing device further to:

perform a simulated radiation treatment delivery based on the set of instructions for the volumetric imager; and provide a notification to a user in response to a collision occurring during the simulated delivery.

21. The non-transitory computer readable medium of claim 20, wherein the processing device is to perform the simulated radiation treatment delivery and provide the notification based on at least one of a change in a couch position or a change in imaging corrections.

* * * * *